(12) United States Patent
Bailly et al.

(10) Patent No.: US 10,138,468 B2
(45) Date of Patent: Nov. 27, 2018

(54) METHOD FOR DIFFERENTIATION OF PLURIPOTENT STEM CELLS INTO MULTI-COMPETENT RENAL PRECURSORS

(71) Applicant: Hoffmann-La Roche Inc., Little Falls, NJ (US)

(72) Inventors: Jacques Bailly, Zimmersheim (FR); Osele Ciampi, Basel (CH); Martin Graf, Zeiningen (CH); Roberto Iacone, Basel (CH); Christoph Patsch, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/010,389

(22) Filed: Jan. 29, 2016

(65) Prior Publication Data

US 2016/0145578 A1    May 26, 2016

Related U.S. Application Data

(63) Continuation of application No. PCT/EP2014/065991, filed on Jul. 25, 2014.

(30) Foreign Application Priority Data

Jul. 29, 2013  (EP) ..................................... 13178342

(51) Int. Cl.
C12N 5/071        (2010.01)

(52) U.S. Cl.
CPC ........ *C12N 5/0687* (2013.01); *C12N 2500/25* (2013.01); *C12N 2500/38* (2013.01); *C12N 2501/155* (2013.01); *C12N 2501/385* (2013.01); *C12N 2501/392* (2013.01); *C12N 2501/727* (2013.01); *C12N 2506/02* (2013.01); *C12N 2506/45* (2013.01)

(58) Field of Classification Search
CPC .................................................. C12N 5/0687
See application file for complete search history.

(56) References Cited

U.S. PATENT DOCUMENTS

| 2007/0031966 A1 | 8/2007 | Dressler et al. | |
|---|---|---|---|
| 2009/0130759 A1* | 5/2009 | Smith ................. | C12N 5/0606 435/455 |

FOREIGN PATENT DOCUMENTS

WO    2012/011610    1/2012

OTHER PUBLICATIONS

Brevini et al., 2010, Theriogenology, vol. 74, pp. 544-550.*
Paris et al. (2010, Theriogenology, vol. 74, pp. 516-524).*
Munoz et al. (2008, Theriogenology, vol. 69, pp. 1159-1164).*
Gomez et al. (2010, Theriogenology, vol. 74, pp. 498-515).*
Jean et al. (2013, Develop. Growth Differ., vol. 55, pp. 41-51).*
Buta et al. (2013, Stem Cell Res., vol. 11, pp. 552-562).*
Batchelder et al. (2009, Differentiation, vol. 78, pp. 45-56).*
Kuure et al. (2007, J. Am. Soc. Nephrol., vol. 18, pp. 1130-1139).*
Watanabe et al. (2007, Nature Biotechnology, vol. 25(6), pp. 681-686).*
Song et al. (2011, J. Am. Soc. Nephrol., vol. 22, pp. 1213-1220).*
Lasagni et al. (2010, Stem Cells, vol. 28, pp. 1673-1685).*
Batchelder et al., "Renal ontogeny in the rhesus monkey(*Macaca mulatta*) and directed differentiation of human embryonic stem cells towards kidney precursors" Differentiation 78:45-56 ( 2009).
Harari-Steinberg et al., "Indentification of human nephron progenitors capable of generation of kidney structures and functional repair of chronic renal disease" EMBO Molecular Medicine 5:1556-1568 ( 2013).
Kobayashi et al., "Six2 Defines and Regulates a Multipotent Self-Renewing Nephron Progenitor Population throughout Mammalian Kidney Development" Cell Stem Cell 3:169-181 ( 2008).
Kuure et al., "Glycogen Synthase Kinase-3 Inactivation and Stabilization of β-Catenin Induce Nephron Differentiation in Isolated Mouse and Rat Kidney Mesenchymes" Journal of the American Society of Nephrology 18:1130-1139 ( 2007).
Morizane et al., "Differentiation of Murine Embryonic Stem and Induced Pluripotent Stem Cells to Renal Lineage in vitro" Biochemical and Biophysical Research Communications 390:1334-1339 ( 2009).
Song et al., "The Directed Differentiation of Human iPS Cells into Kidney Podocytes" PLOS One 7(9):e46453 ( 2012).

* cited by examiner

*Primary Examiner* — Thaian N Ton
*Assistant Examiner* — David A. Montanari
(74) *Attorney, Agent, or Firm* — Grant Kalinowski

(57) ABSTRACT

This application relates to a method for differentiating pluripotent stem cells (PSCs) into multi-competent renal precursor cells expressing Six2. These renal precursor cells are able to differentiate into fully functional and fully differentiated podocytes. Moreover this application relates to a method for differentiating human embryonic stem cells (ESCs) and induced pluripotent stem cells (iPSCs) into defined renal precursor cells expressing Six2 and podocytes based on linked steps of chemically defined medium inductions.

11 Claims, 12 Drawing Sheets

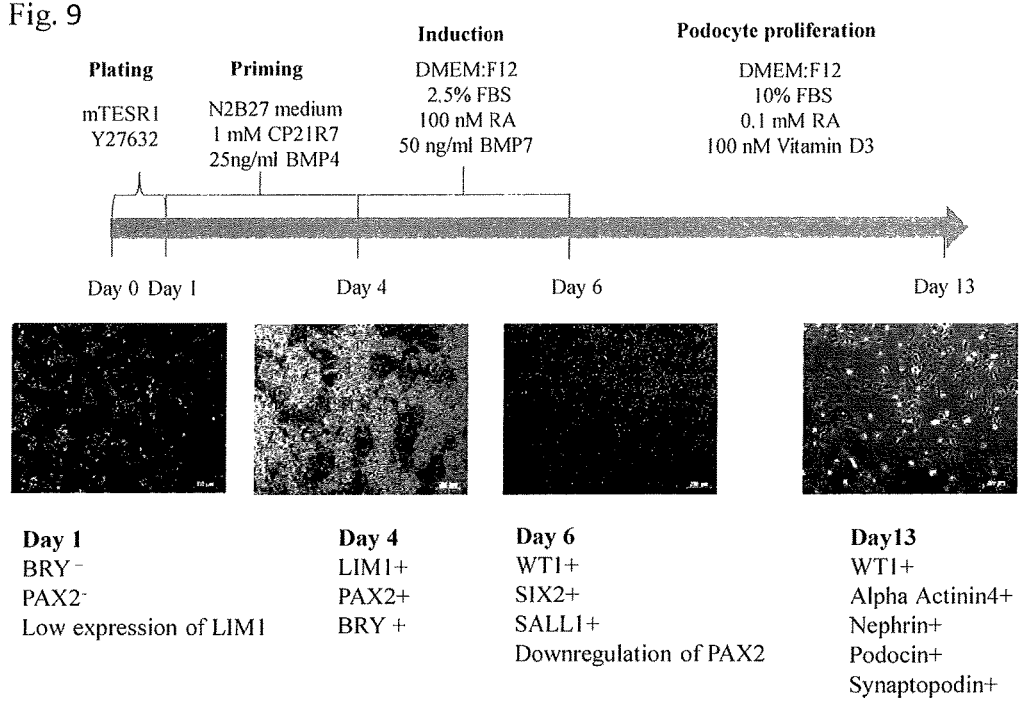

Figure 1:
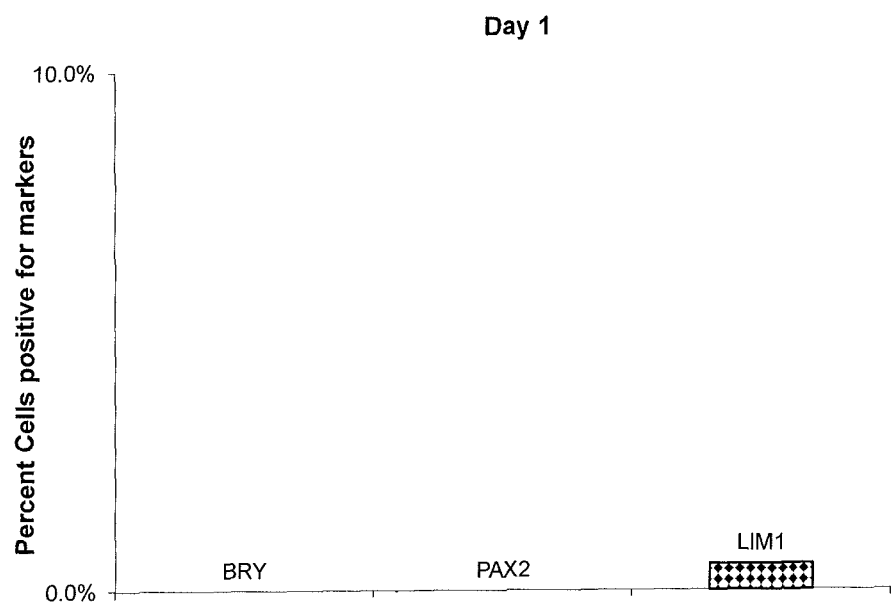

METHOD FOR DIFFERENTIATION OF PLURIPOTENT STEM CELLS INTO MULTI-COMPETENT RENAL PRECURSORS

RELATED APPLICATIONS

This application is a continuation of International Application No. PCT/EP2014/065991, filed Jul. 25, 2014, which claims the benefit of priority under 35 USC 119(a) to European patent application number 13178342.5, filed Jul. 29, 2013, the disclosure of each of which is incorporated herein by reference in its entirety.

FIELD OF THE INVENTION

This application relates to a method for differentiating pluripotent stem cells (PSCs) into defined multi-competent renal precursor cells expressing Six2. These renal precursor cells are able to differentiate into fully functional and fully differentiated podocytes. Moreover this application relates to a method for differentiating human embryonic stem cells (ESCs) and induced pluripotent stem cells (iPSCs) into defined renal precursor cells expressing Six2 and podocytes based on linked steps of chemically defined medium inductions.

BACKGROUND

Renal cells are used in basic research, disease models, tissue engineering, drug screening, and in vitro toxicology. The kidneys have highly differentiated and complicated structures, and have pivotal roles in many physiological processes, such as body fluid osmolality, regulation of fluid and electrolyte balance, regulation of acid-base balance, excretion of metabolic waste products and foreign chemicals, and production of hormones controlling blood pressure and erythropoiesis. Once damaged, kidneys rarely recover their functions. Renal cells (e.g. Podocytes and tubular cells) can regenerate to some extent following acute necrosis. However, kidneys generally do not regenerate in patients with chronic kidney diseases (Humphreys and Bonventre, 2007), leading to end-stage renal insufficiency. Chronic kidney disease (CKD) is a major cause of morbidity and mortality affecting 11% of the adult population in Western countries. People with CKD suffer from a substantial loss of quality of life. The pharmacoeconomic burden caused by this disease is very high, as there is a permanent shortage of donor kidneys for transplantation.

The mammalian kidney is derived from the intermediate mesoderm (IM), which gives rise to the nephric duct (ND) and the metanephric mesenchyme (MM). The ND gives rise to the collecting duct system, which is composed of two key cell types, principal cells, and intercalated cells. The MM specifies the cap mesenchyme (CM) and also gives rise to the stroma. The CM is the nephron progenitor population and differentiates in the renal vesicle via a mesenchyme-to-epithelial transition.

The nephron consists of a glomerular tuft or glomerulus, and a renal tubule. The glomerulus is a highly specialized filtration unit that separates waste products for excretion as urine. The filtration barrier between blood and urine in the glomerulus is provided by highly specialized, terminally differentiated cells termed podocytes.

Converging evidence suggests that damage to the podocytes is one of the key events triggering loss of renal function. Podocyte damage occurs secondary to hyperinsulinemia, hemodynamic mechanisms and other mechanisms. The progressive loss of podocytes leads to broad sclerosis of the glomeruli accompanied by increased proteinuria and reduction in the clearance function (Wiggins, 2007).

However, the underlying mechanisms of insulin resistance and loss of regenerative properties leading to pathophysiological changes in the nephron of the kidney are not completely understood. Thus there is a need for in vitro cell models to study the biology of renal diseases like CKD and to facilitate the development of new treatments.

Embryonic stem (ES) cells and patient specific induced pluripotent stem cells (iPSCs) are a potential source for the production of renal precursor cells and podocytes in large scale for regenerative medicine and disease modeling for drug discovery. With the induced pluripotent stem cells (iPSCs) technology (Takahashi, K. & Yamanaka, S., "Induction of pluripotent stem cells from mouse embryonic and adult fibroblast cultures by defined factors", Cell 126, 663-676 (2006)) somatic cells can be reprogrammed to iPSCs by transduction of four defined factors (Sox2, Oct4, Klf4, c-20 Myc). The iPSC technology enables the generation of patient specific iPSCs, which can be differentiated into patient specific renal cells. These patient specific renal cells are useful for example in vitro modeling of the pathophysiology of renal disease such as Chronic Kidney Disease (CKD), Focal segmental glomerulosclerosis (FSGS), Membranoproliferative glomerulonephritis, Polycystic kidney disease (PKD) and diabetic nephropathy associated with Diabetes Type-2, or for the assessment of drug toxicity. One important prerequisite to attempt such in vitro disease modeling is the implementation of an efficient, robust and scalable differentiation system (Tiscornia et al., 2011).

Previous efforts to differentiate human PSCs into renal cells have not achieved scales and efficacies relevant for drug discovery campaigns or regenerative cell therapies, neither in humans (Batchelder et al., 2009; Lin et al., 2010; Mae et al., 2013; Narayanan et al., 2013; Song et al., 2012) or mice (Kim and Dressler, 2005; Mae et al., 2010; Morizane et al., 2009; Nishikawa et al., 2012; Ren et al., 2010). In addition, a major concern is the mal-differentiation of the cells into unwanted tissues or even the formation of teratomas. To avoid this danger, one must direct the cells to a state of differentiation that will on the one hand provide them with the potential to regenerate mature kidney cells of interest and on the other hand prevent mal-differentiation. This can be achieved by the controlled activation of the correct network of nephric transcription factors. Unfortunately, attaining this exact state of differentiation in vitro has proven to be quite difficult. Many attempts have been made to induce pluripotent cells in this manner, applying both growth factor combinations [bone morphogenetic protein (BMP)/Activin/Retinoic acid] and genetic approaches. However, most differentiation studies, even after successfully inducing renal lineage genes, failed to pinpoint the exact stage in nephrogenesis (IM, MM, CM) to which ESCs were differentiated along the renal lineage.

Therefore, a highly efficient and chemically defined method for stimulating the differentiation of human pluripotent stem cells into kidney lineages remains to be developed.

Mae et al. 2013 describe a protocol to differentiate human pluripotent stem cells into intermediate mesoderm cells which express Osr1 using defined induction steps in serum free media. The authors dissociated the undifferentiated cells with Accutase® to obtain a single layer of cells and induced the differentiation with Activin A, a GSK3 beta inhibitor and a ROCK kinase inhibitor in a first step and BMP7 and the GSK3 beta inhibitor in a second step. The authors obtained 90% Osr1 positive cells on day 11 only. Expression of PAX2, LIM1, WT1, CITED2, EYA1 and SALL1 (marker genes for the developing kidney, gonad and adrenal cortex) was observed after 18 days, indicating that the authors obtained a heterogeneous cell population of different cell types and cells in different differentiation stages.

Lin et al., 2010 describe the differentiation of human embryonic stem cells into mesodermal renal progenitor lineages by reducing serum concentration and feeder layer density for 14 days. The authors obtained a heterogeneous population of differentiated human embryonic cells which they fractionated by flow cytometry.

Batchelder et al., 2009 describe the direct differentiation of embryonic stem cells towards the renal lineage by culturing the embryonic stem cells with retinoic acid, activin A, BMP7 or BMP4 on laminin or gelatin substrates in a monolayer. They obtained cells with upregulated intermediate mesoderm marker genes (PAX2, SIX2, WT1 and OSR1) at day 4. However, markers for kidney precursors and markers of undifferentiated cells were also elevated at day 4. Batchelder et al do not show any further differentiation of this heterogeneous population into defined cell types. The differentiation of the embryonic stem cells is achieved through a stage with embryoid bodies, which generally limits reproducibility and standardization of the protocol.

Hence, prior art protocols for differentiation of human pluripotent stem cells into kidney percursors have major drawbacks: Firstly, most protocols result in a heterogenous population of cells and the absolute yield of defined renal precursor cells stably expressing metanephric mesenchyme markers is very low. In addition, the overall time needed to differentiate pluripotent stem cells into renal precursor cells by most known methods is very long. Many protocols require undefined elements such as medium conditioned with factors secreted by primary cells, co-cultures with feeder layers, which limit the standardization of these methods. In addition, many protocols rely on cell aggregates or embryoid bodies, which due to their heterogeneous nature constrain the reproducibility of these techniques.

Song et al. 2012 is the first reported protocol to differentiate human induced pluripotent stem cells into kidney podocytes. Following ten days of directed differentiation in medium supplemented with fetal bovine serum and different growth factors (BMP7, Activin-A and retinoic acid), the authors obtained iPS cells with a podocyte phenotype. They obtained cells expressing podocyte specific genes but also still expressing the metanephric mesenchymal genes PAX2 and WT1, indicating that the obtained podocytes are immature and not fully differentiated. Song et al do not describe any of the intermediate stages of the differentiation like the intermediate mesoderm or the metanephric mesenchyme.

None of the known protocols provide defined renal precursor cells that express Six2, WT1, and SALL1 with downregulation of the expression of PAX2, i.e. defined metanephric mesenchyme cells. None of the known protocols describe the differentiation of the renal precursor cell into podocytes.

In summary, there is no method that provides a defined population of renal precursor cells expressing metanephric mesenchyme markers at very high yield after only six days. In addition none of the known protocols provides fully functional and fully differentiated podocytes at very high yield after only 13 days.

SUMMARY OF THE INVENTION

The present invention provides an improved method for differentiating pluripotent stem cells into a defined metanephric mesenchyme renal precursor stage in a shorter amount of time (6 days) and with a significantly increased yield (up to 95% yield of renal precursor cells expressing marker genes SIX2, SALL1 and WT1) compared to prior art protocols. The new method alleviates the necessity of obtaining embryoid bodies or small cell clumps from pluripotent stem cells and removes the major drawback of low reproducibility and standardization of methods known so far. Moreover, the high efficiency allows the use of these defined precursor cells in large scales in drug discovery and safety assessments, in regenerative medicine applications, and in in vitro disease modeling in the pharmaceutical industry. In addition, the new method permits the selective modulation of the metanephric mesenchyme renal precursor cells, which enables shifting lineage commitment into fully differentiated podocytes (~99%) after 13 days.

Provided herein is a method for differentiating pluripotent stem cells into renal precursor cells expressing SIX2, the method comprising the steps of:
a) providing a monolayer of pluripotent stem cells in a pluripotency medium
b) incubating the cells in a priming medium supplemented with a small molecule inhibitor of glycogen synthase kinase 3 (Gsk3a-b),
c) inducing the differentiation by incubating the primed cells in an induction medium.

In one embodiment the renal precursor cells express the additional marker genes WT1 and/or SALL1.

In one embodiment the small molecule inhibitor of glycogen synthase kinase 3 (Gsk3a-b) is 3-(3-Amino-phenyl)-4-(1-methyl-1H-indol-3-yl)-pyrrole-2,5-dione.

In one embodiment the pluripotency medium of step a) is a serum-free medium supplemented with an inhibitor of the Rho-associated coiled-coil forming protein serine/threonine kinase family of protein kinases (ROCK kinase inhibitor).

In one embodiment the ROCK kinase inhibitor is selected from the group of 1-(5-Isoquinolinesulfonyl)homopiperazine), N-Benzyl-2-(pyrimidin-4-ylamino)thiazole-4-carboxamide) and (+)-(R)-trans-4-(1-aminoethyl)-N-(4-pyridyl)cyclo-hexanecarboxamide dihydrochloride).

In one embodiment the priming medium of step b) is a serum free medium supplemented with insulin, transferrin and progesterone.

In one embodiment the priming medium of step b) additionally comprises recombinant bone morphogenic protein-4 (BMP4).

In one embodiment step a) comprises incubating the cells in the pluripotency medium for 18 hours to 30 hours.

In one embodiment step b) comprises incubating the cells in the priming medium for 2 to 4 days.

In one embodiment step c) comprises incubating the cells in the induction medium for 18 hours to 48 hours.

In one embodiment the induction medium is a serum-free medium supplemented with recombinant bone morphogenic protein-7 (BMP7).

In one embodiment the induction medium is a serum-free medium supplemented with Retinoic Acid.

In one embodiment the method additionally comprises step
d) incubating the product of step c) under conditions suitable for proliferation of the podocytes.

In one embodiment the pluripotent stem cell is an induced pluripotent stem cell.

In one embodiment the induced pluripotent stem cell is a human cell.

In one embodiment the induced pluripotent stem cell is obtained from a subject suffering from a renal disease.

In one embodiment renal precursor cells expressing SIX2 or differentiated podocytes obtained by a method according to any of the embodiments described herein is provided.

In one embodiment a biobank of renal precursor cells expressing SIX2 or differentiated podocytes obtained by a method according to any of the embodiments described herein is provided.

In one embodiment use of renal precursor cells expressing SIX2 or differentiated podocytes obtained by a method according to any of the embodiments described herein or of the biobank of of renal precursor cells expressing SIX2 or differentiated podocytes obtained by a method according to any of the embodiments described herein as in vitro model for renal diseases is provided.

In one embodiment a therapeutic composition comprising renal precursor cells expressing SIX2 or differentiated podocytes obtained by a method according to any of the embodiments described herein or of the biobank of of renal precursor cells expressing SIX2 or differentiated podocytes obtained by a method according to any of the embodiments is provided.

Any of the above embodiments may be present singly or in combination.

SHORT DESCRIPTION OF THE FIGURES

FIG. 1: Quantification BRY+, PAX2+, LIM1+, iPSCs cells by image based high content analysis (HCA). Human iPS cells have been cultured in monolayer conditions. Quantification graph: Percent BRY+, PAX2+, and LIM1+ positive cells at Day 1 in pluripotency medium. These findings were confirmed by whole genome expression profiling (data not shown).

Figure 2:
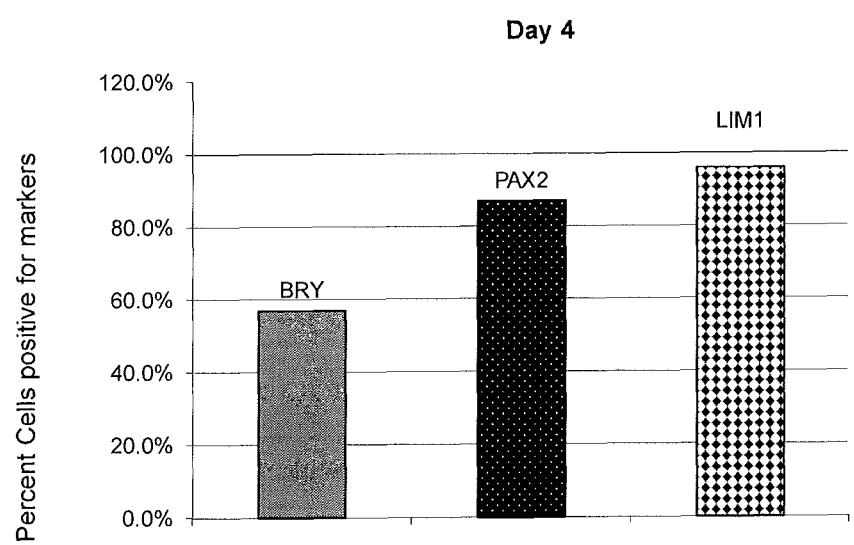

FIG. 2: Quantification BRY+, PAX2+, LIM1+, iPSCs derived cells by image based high content analysis (HCA). Human iPS cells have been differentiated in monolayer conditions. Quantification graph: Percent BRY+, PAX2+, and LIM1+ positive cells at Day 4 in priming medium. These findings were confirmed by whole genome expression profiling (data not shown).

Figure 3:
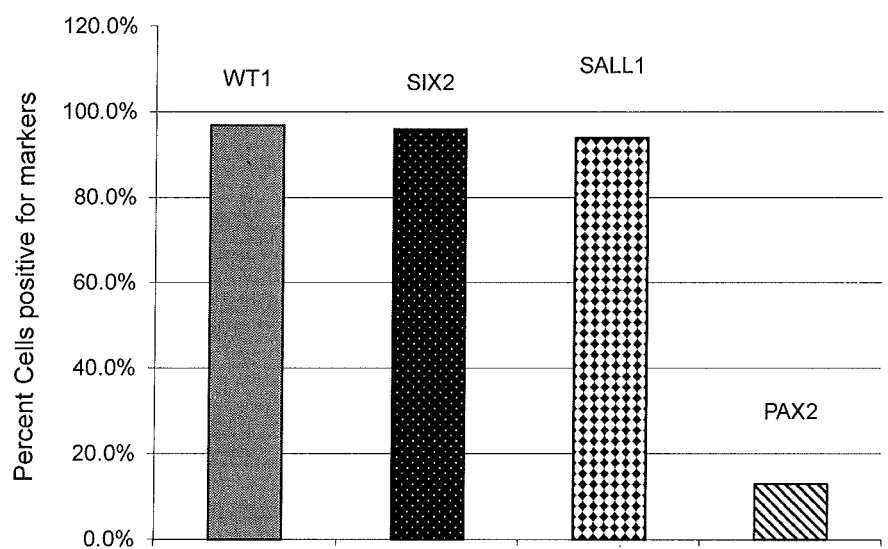

FIG. 3: Quantification WT1+, SIX2+, SALL1+, and PAX2 low, iPSCs derived multi-competent renal precursors by image based high content analysis (HCA). Human iPS cells have been differentiated in monolayer conditions. Main panel: Quantification graph: Percent WT1+, SIX2+, SALL1+, and PAX2+ positive cells at Day 6 in induction medium. These findings were confirmed by whole genome expression profiling (data not shown).

Figure 4:
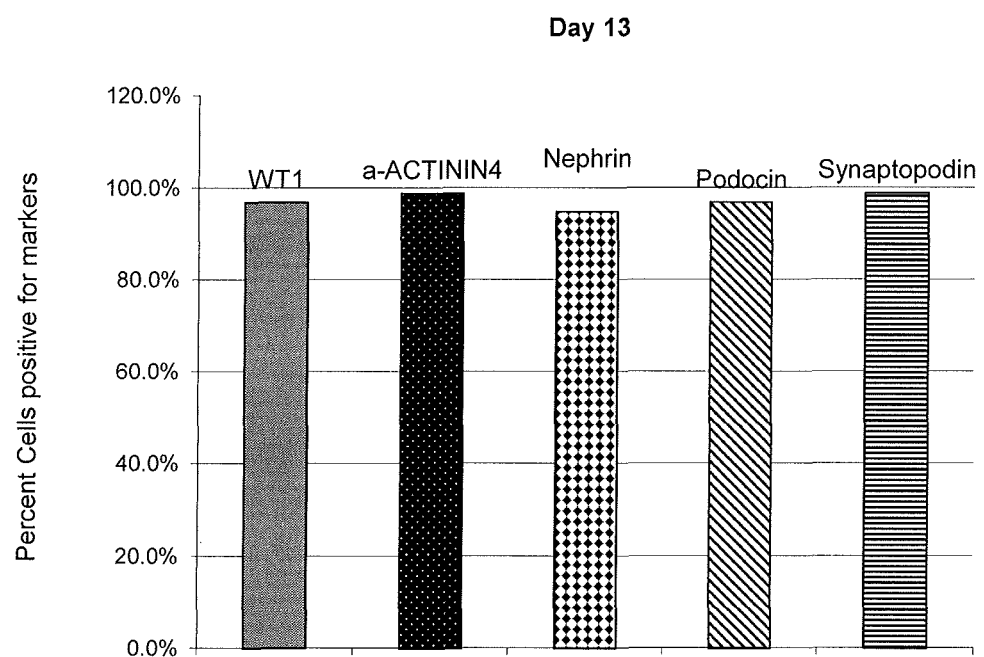

FIG. 4: Quantification WT1+, a-ACTININ4+, NEPRHIN+, PODOCIN+ and SYNAPTOPODIN+, iPSCs derived functional Podocytes by image based high content analysis (HCA). Human iPS cells have been differentiated in monolayer conditions. Main panel: Quantification graph: Percent WT1+, a-ACTININ4+, NEPRHIN+, PODOCIN+ and SYNAPTOPODIN+ positive cells at Day 13 in Podocytes proliferation medium. These findings were confirmed by whole genome expression profiling (data not shown).

Figure 5:
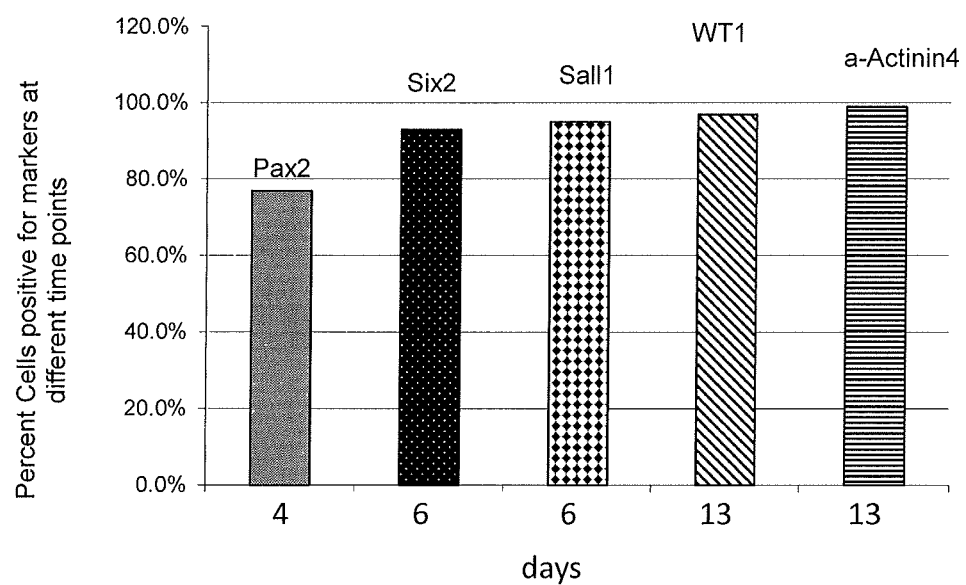

FIG. 5: Reproducibility of the Podocytes cell differentiation method using as starting hESCs. Image based high content analysis (HCA) quantification of key markers regulated during the Podocytes cell differentiation method. The human embryonic stem cell line (SA001 from Cellartis) has been differentiated in monolayer conditions. Main panel: Quantification graph: Percent PAX2+ positive cells at Day 4 in priming medium; SIX2+ and SALL1+ positive cells at Day 6 in induction medium; WT1+, and a-ACTININ4+ positive cells at Day 13 in Podocytes proliferation medium.

Figure 6:
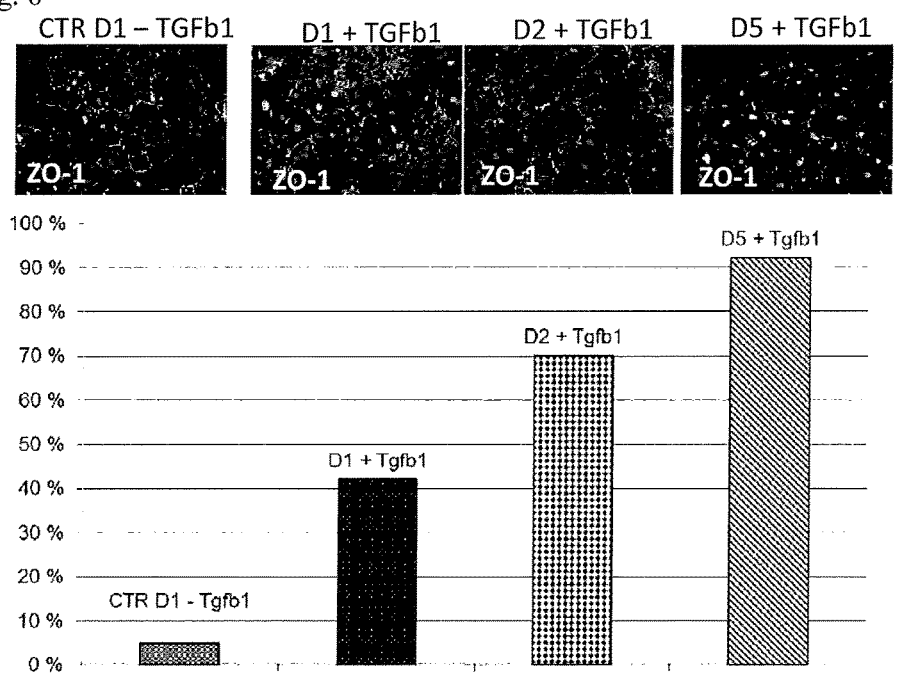

FIG. 6: Characterization of monolayer differentiated hPSCs-derived Podocytes cells at Day 13. hiPSCs have been differentiated in monolayer conditions and at Day 13 have been tested for functional response to TGF beta (10 ng/ml) stressor stimulation. The expression of the tight junction marker ZO-1 has been tested by immunocytochemistry analysis and its cellular localization by image based high content analysis (HCA). Upper panel: Representative images ZO-1 immunocytochemistry where it is show a defined ZO-1 localization at the membrane for Day 1 in DMEMF12 Medium without TGF Beta (CTR D1-TGFb1), upon TGF beta stimulation we report a remodeling and translocation of the ZO-1 expression form the membrane to the perinuclear zone already at Day 1 (D1+TGFb1), and it is sustained over time by the continuous stimulation with TGF beta (D2+TGFb1 and (D5+TGFb1). Lower panel: Quantification graph: Percent positive cells for perinuclear translocation of ZO-1 expression in podocytes at different days.

Figure 7:
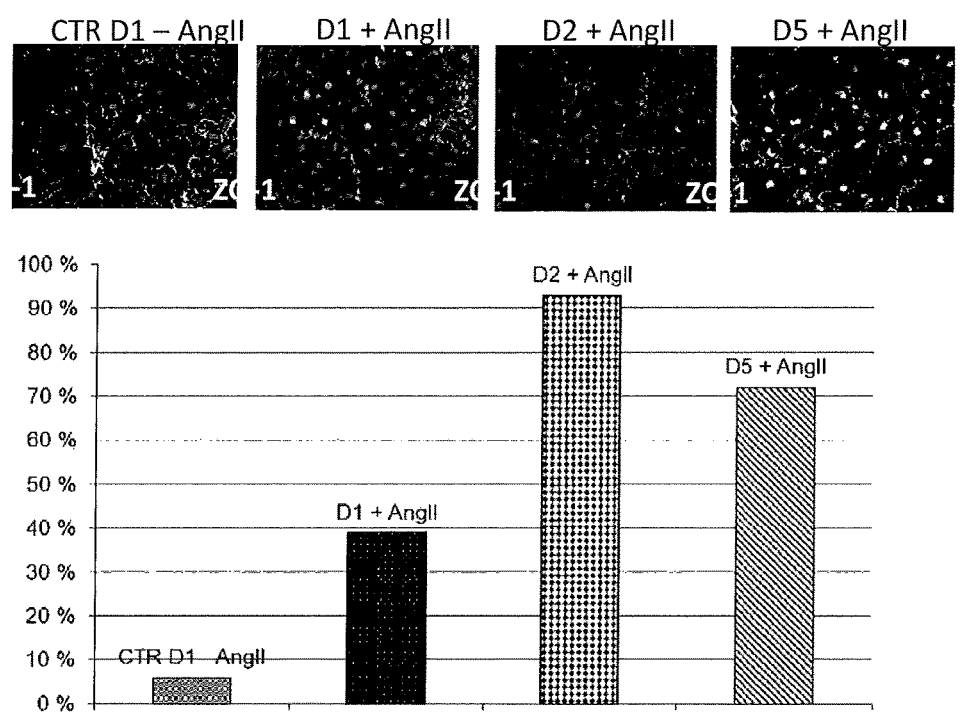

FIG. 7: Characterization of monolayer differentiated hPSCs-derived Podocytes cells at Day 13. hiPSCs have been differentiated in monolayer conditions and at Day 13 have been tested for functional response to Angiotensin II (AngII) (100 nM) stressor stimulation. The expression of the tight junction marker ZO-1 has been tested by immunocytochemistry analysis and its cellular localization by image based high content analysis (HCA). Upper panel: Representative images ZO-1 immunocytochemistry where it is show a defined ZO-1 localization at the membrane for Day 1 in DMEMF12 Medium without AngII (CTR D1−AngII), upon AngII stimulation we report a remodeling and translocation of the ZO-1 expression form the membrane to the perinuclear zone already at Day 1 (D1+AngII), and it is sustained over time by the continuous stimulation with AngII (D2+AngII and (D5+AngII). Lower panel: Quantification graph: Percent positive cells for perinuclear translocation of ZO-1 expression in podocytes at different days.

Figure 8:
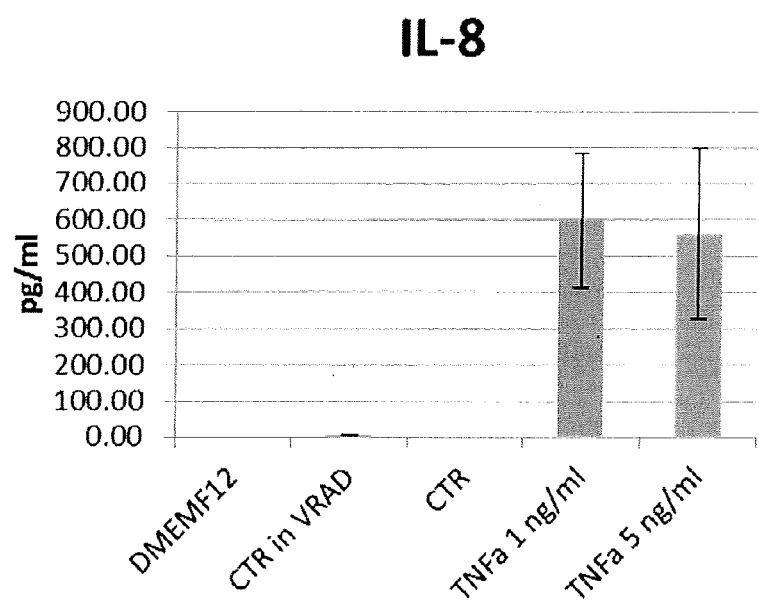
Figure 8:
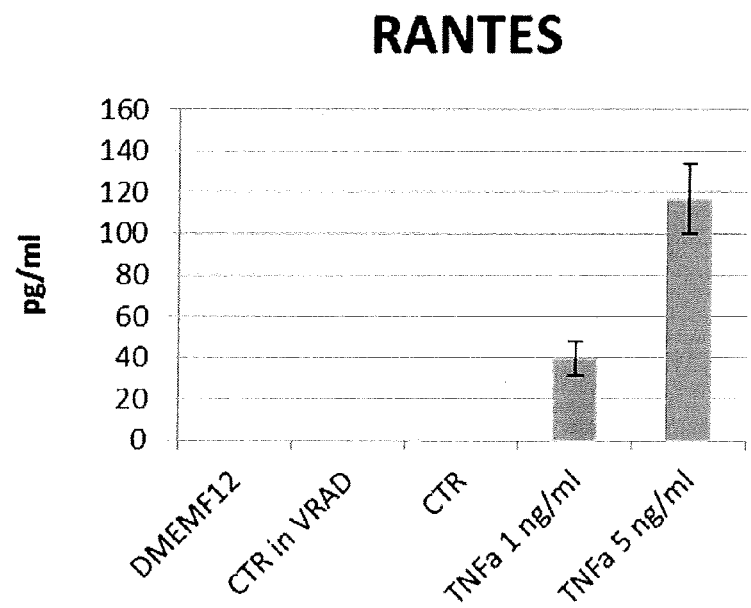
Figure 8:
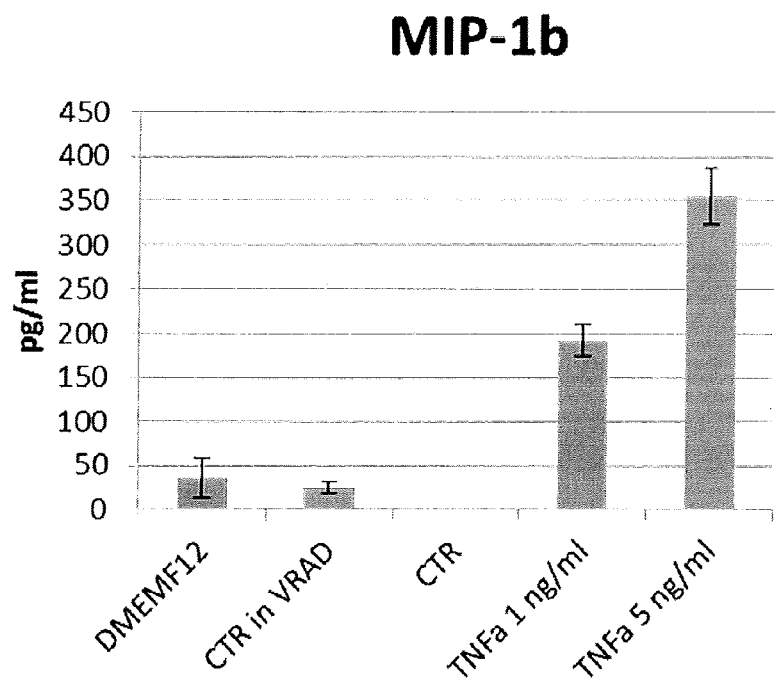
Figure 8:
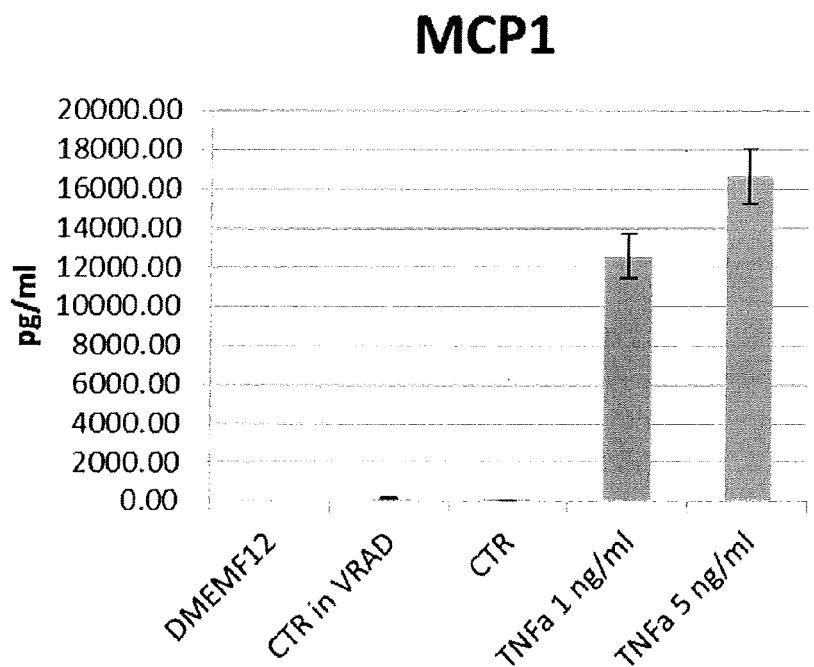

FIG. 8a: Pro-inflammatory cytokine response assay. hPSCs-derived Podocytes cells at Day 13 upregulate the expression of pro-inflammatory markers such as IL-8 upon stimulation with TNFα (1 ng/ml and 5 ng/ml) after 24 h in DMEMF12 medium Main panel: Quantification graph: concentration in the harvested supernatant (pg/ml) of the mentioned cytokines. Bio-Plex Pro Cytokine, Chemokine and Growth factor assay was used to measure the activation of hPSCs-derived Podocytes cells in response to TNFα. The secreted cytokines were significantly upregulated (quantification graphs).

FIG. 8b: Pro-inflammatory cytokine response assay. hPSCs-derived Podocytes cells at Day 13 upregulate the expression of pro-inflammatory markers such as RANTES upon stimulation with TNFα (1 ng/ml and 5 ng/ml) after 24 h in DMEMF12 medium Main panel: Quantification graph: concentration in the harvested supernatant (pg/ml) of the mentioned cytokines. Bio-Plex Pro Cytokine, Chemokine and Growth factor assay was used to measure the activation of hPSCs-derived Podocytes cells in response to TNFα. The secreted cytokines were significantly upregulated (quantification graphs).

FIG. 8c: Pro-inflammatory cytokine response assay. hPSCs-derived Podocytes cells at Day 13 upregulate the expression of pro-inflammatory markers such as MIP1b upon stimulation with TNFα (1 ng/ml and 5 ng/ml) after 24 h in DMEMF12 medium Main panel: Quantification graph: concentration in the harvested supernatant (pg/ml) of the mentioned cytokines. Bio-Plex Pro Cytokine, Chemokine and Growth factor assay was used to measure the activation of hPSCs-derived Podocytes cells in response to TNFα. The secreted cytokines were significantly upregulated (quantification graphs).

FIG. 8d: Pro-inflammatory cytokine response assay. hPSCs-derived Podocytes cells at Day 13 upregulate the expression of pro-inflammatory markers such as MCP1 upon stimulation with TNFα (1 ng/ml and 5 ng/ml) after 24 h in DMEMF12 medium Main panel: Quantification graph: concentration in the harvested supernatant (pg/ml) of the mentioned cytokines. Bio-Plex Pro Cytokine, Chemokine and Growth factor assay was used to measure the activation of hPSCs-derived Podocytes cells in response to TNFα. The secreted cytokines were significantly upregulated (quantification graphs).

FIG. 9: Schematic representation of the method for differentiating human pluripotent stem cells (PSCs) to Podocytes. Day 0: human PSCs were enzymatically dissociated and plated on pre-coated Matrigel® plates using a concentration of 37000 cells/cm' in pluripotency medium (mTeSR1™ with Y27631 10 µM). Day 1: Media change with fresh priming medium (N2B27 with Compound 21 (CP21R7) 1 µM and 25 ng/ml BMP4). Day 4: Media change with fresh induction medium (DMEMF12 with 2.5% FBS, 100 nM Retinoic Acid and 50 ng/ml BMP7). Day 6: The cells are detached with Accutase® and after centrifugation plated in collagen I coated plates using a concentration of 50000 cells/cm$^2$ in Podocytes proliferation medium (DMEMF12 with 10% FBS, 0.1 mM Retinoic Acid and 100 nM Vitamin D3). At Day 13 Podocytes cells are shown.

DETAILED DESCRIPTION OF THE INVENTION

The present invention provides an improved method for differentiating pluripotent stem cells into a defined metanephric mesenchyme renal precursor stage in a shorter amount of time (6 days) and with a significantly increased yield (up to 95% yield of renal precursor cells expressing marker genes SIX2, SALL1 and WT1) compared to prior art protocols. The renal precursor cells express SIX2, SALL1 and WT1, which are all important markers of the metanephric mesenchyme. SIX2, also known as SIX homeobox 2 (NCBI Gene ID: 10736), is a member of the vertebrate gene family which encode proteins homologous to the *Drosophila* 'sine oculis' homeobox protein. The encoded protein is a transcription factor which has an important role for metanephros development. SIX2 is an important marker of the metanephric mesenchyme (see e.g. Nishinakamura et al, 2011 and Chai et al, 2013). SALL1 (full name: SALL1 sal-like 1 (*Drosophila*) [*Homo sapiens* (human)] NCBI Gene ID: 6299), is also known as TBS; HSAL1; Sal-1; ZNF794. The protein encoded by this gene is a zinc finger transcriptional repressor and is highly expressed in multipotent nephron progenitors in the mesenchyme (Nishinakamura et al, 2011). WT1 (full name: Wilms tumor 1, also known as GUD; AWT1; WAGR; WT33; NPHS4; WIT-2; EWS-WT, NCBI Gene ID:7490) encodes a transcription factor that contains four zinc-finger motifs at the C-terminus and a proline/glutamine-rich DNA-binding domain at the N-terminus. It has an essential role in the normal development of the urogenital system, and it is mutated in a small subset of patients with Wilm's tumors. WT1 is an important marker of the metanephric mesenchyme (see e.g. Chai et al, 2013).

In addition to obtaining defined metanephric mesenchyme renal precursor cells, the new method permits the selective modulation of the metanephric mesenchyme renal precursor cells, which enables shifting lineage commitment into fully differentiated podocytes (~99%) after 13 days.

Provided herein is a method for differentiating pluripotent stem cells into renal precursor cells expressing SIX2, the method comprising the steps of:
a) providing a monolayer of pluripotent stem cells in a pluripotency medium
b) incubating the cells in a priming medium supplemented with a small molecule inhibitor of glycogen synthase kinase 3 (Gsk3a-b),
c) inducing the differentiation by incubating the primed cells in an induction medium.

In one embodiment the renal precursor cells are metanephric mesenchyme cells. In one embodiment the renal precursor cells express the additional marker genes WT1 and/or SALL1. In one embodiment the renal precursor cells express WT1, SALL1 and SIX2. In another embodiment the renal precursor cells downregulate marker genes of the intermediate mesoderm. Hence, in one embodiment the renal precursor cell express PAX2 only at a very low level. PAX2 (full name Paired Box 2, NCBI Gene ID 5076, also known as PAPRS) encodes paired box gene 2, one of many human homologues of the *Drosophila melanogaster* gene prd. The central feature of this transcription factor gene family is the conserved DNA-binding paired box domain. PAX2 is an important marker of the intermediate mesoderm (Chai et al, 2013, Nishikawa et al, 2012) and is downregulated in the metanephric mesenchyme. In one embodiment the renal precursor cells do not express LIM1 and/or BRY. LIM1 (official symbol LHX1, full name LIM homeobox 1, NCBI Gene ID 3975) encodes a member of a large protein family which contains the LIM domain, a unique cysteine-rich zinc-binding domain. The encoded protein is a transcription factor important for the development of the renal and urogenital systems: LIM1 is a marker for nephrogenic intermediate mesoderm (Nishikawa et al, 2012). The protein product of the T gene (full name: T, brachyury homolog (mouse) [*Homo sapiens* (human)] NCBI Gene ID: 6862, herein referred to as "BRY"), Brachyury, is an embryonic nuclear transcription factor and widely used as the definitive benchmark for mesodermal differentiation (Nishikawa et al, 2012).

Preferably the media are changed in between each steps, that means that the first medium is discarded e.g. by aspiration before the second medium is added to the cells.

"A monolayer of pluripotent cells" as used herein means that the pluripotent stem cells are provided in single cells which are attached to the adhesive substrate in one single film, as opposed to culturing cell clumps or embryoid bodies in which a solid mass of cells in multiple layers form various three dimensional formations attached to the adhesive substrate.

Providing a monolayer of pluripotent stem cells in the initial step is crucial for the reproducibility and efficiency of the method. In one embodiment, monolayers of pluripotent stem cells can be produced by enzymatically dissociating the cells into single cells and bringing them onto an adhesive substrate, such as pre-coated Matrigel® plates (e.g. BD Matrigel® hESC-qualified from BD Bioscience, Geltrex hESC-qualified from Invitrogen, Synthemax from Corning). Examples of enzymes suitable for the dissociation into single cells include Accutase® (Invitrogen), Trypsin 25 (Invitrogen), TrypLe™ Express (Invitrogen). In one embodiment, 20000 to 60000 cells per cm2 are plated on the adhesive substrate. The medium used herein is a pluripotency medium which facilitates the attachment and growth of the pluripotent stem cells as single cells in a monolayer.

"Pluripotency medium" as used herein refers to any chemically defined medium useful for the attachment of the pluripotent stem cells as single cells on a monolayer while maintaining their pluripotency and are well known in the art. In one embodiment the pluripotency medium comprises at least one of the following growth factors: basic fibroblast growth factor (bFGF, also depicted as Fibroblast Growth Factor 2, FGF2) and transforming growth factor β (TGFβ). In one embodiment, the pluripotency medium is a serum free medium supplemented with a small molecule inhibitor of the Rho-associated coiled-coil forming protein serine/threonine kinase (ROCK) family of protein kinases (herein referred to as ROCK kinase inhibitor).

Thus, in one embodiment, step a) of the method described above comprises providing a monolayer of pluripotent stem cells in a pluripotency medium, wherein the pluripotency medium is a serum free medium supplemented with a ROCK kinase inhibitor.

Examples of serum-free pluripotency media suitable for the attachment are mTeSR1™ or TeSR2 from Stem Cell Technologies, Primate ES/iPS cell medium from Repro-CELL and StemPro® hESC SFM from Invitrogen, X-VIVO™ from Lonza, Stemline Pluripotent Stem Cell Culture Medium from Sigma Aldrich, NutriStem™ XF/FF Culture Medium from Stemgent, Essential 8™ Medium (prototype) from Invitrogen and STEMium® from Scien-Cell Research Laboratories.

Examples of ROCK kinase inhibitor useful herein are Fasudil (1-(5-Isoquinolinesulfonyl)homopiperazine), Thiazovivin (N-Benzyl-2-(pyrimidin-4-10 ylamino)thiazole-4-carboxamide) and Y27632 ((+)-(R)-trans-4-(1-aminoethyl)-N-(4-pyridyl)cyclo-hexanecarboxamide dihydrochloride, e.g. Catalogue Number: 1254 from Tocris bioscience). In one preferred embodiment the ROCK kinase inhibitor is Y27632. In one embodiment, the pluripotency medium is a serum free medium supplemented with 2-20 μM Y27632, preferably 5-10 μM Y27632. In another embodiment the pluripotency medium is a serum free medium supplemented with 2-20 μM Fasudil. In another embodiment the pluripotency medium is a serum free medium supplemented with 0.2-10 μM Thiazovivin.

In one embodiment step a) of the method described above comprises providing a monolayer of pluripotent stem cells in a pluripotency medium and incubating (growing) the monolayer in the pluripotency medium for one day (24 hours). In another embodiment step a) of the method described above comprises providing a monolayer of pluripotent stem cells in a pluripotency medium and incubating the monolayer in the pluripotency medium for 18 hours to 30 hours, preferably for 23 to 25 hours.

In another embodiment step a) of the method described above comprises providing a monolayer of pluripotent stem cells in a pluripotency medium, wherein the pluripotency medium is a serum-free medium supplemented with a ROCK kinase inhibitor, and incubating the monolayer in the pluripotency medium for one day (24 hours). In another embodiment step a) of the method described above comprises providing a monolayer of pluripotent stem cells in a pluripotency medium, wherein the pluripotency medium is a serum-free medium supplemented with a ROCK kinase inhibitor, and incubating the monolayer in the pluripotency medium for 18 hours to 30 hours, preferably for 23 to 25 hours.

A "suitable medium for priming", also depicted as "priming medium", as used herein refers to any chemically defined medium useful for priming of the pluripotent stem cells towards renal precursor cells. As used herein, "priming medium" refers to a medium that comprises at least one factor, such as a small molecule that activates the Beta-Catenin (cadherin-associated protein, beta 1; human gene name CTNNB1) pathway and/or the Wnt receptor signaling pathway and/or hedgehog (HH) signaling pathway, that promotes the induction activity of intermediate mesoderm. In one preferred embodiment the priming medium comprises a small molecule inhibitor of glycogen synthase kinase 3 (Gsk3a-b). In one embodiment the a small molecule inhibitor of glycogen synthase kinase 3 (Gsk3a-b) is 3-(3-Amino-phenyl)-4-(1-methyl-1H-indol-3-yl)-pyrrole-2,5-dione.

Upon incubation in priming medium, the pluripotent stem cells start to change cell morphology overtime and the cell proliferation is increased. The "priming" step is defined by the expression of specific genes and markers involved into the intermediate mesoderm transition (e.g. upregulation of BRY, PAX2, LIM1, GATA2, VIMENTIN, SMA, HAND1, KDR and FOXa2 (low expression)) and down regulation of the pluripotency associated genes and markers (e.g. OCT4 (POU5F1), NANOG, SOX2, REX1 (ZFP42), LEFTY1, LEFTY2, TDGF1, DNMT3B, GABRB3, GDF3, TERT, see e.g. Tan et al, 2007).

In one embodiment the small molecules activating Beta-Catenin (cadherin-associated protein, beta 1; human gene name CTNNB1) pathway and/or the Wnt receptor signaling pathway and/or hedgehog (HH) signaling pathway are selected from the group consisting of small molecule inhibitors of glycogen synthase kinase 3 (Gsk3a-b), small molecule inhibitors of CDC-like kinase 1 (Clk1-2-4), small molecule inhibitors of mitogen-activated protein kinase 15 (Mapk15), small molecule inhibitors of dual-specificity tyrosine-(Y)-phosphorylation regulated kinase (Dyrk1a-b 4), small molecule inhibitors of cyclin-dependent kinase 16 (Pctk1-3 4), Smoothened (SMO) activators and modulators of the interaction between β-catenin (or γ-catenin) 15 and the coactivator proteins CBP (CREB binding protein) and p300 (E1A binding protein p300).

Preferably the glycogen synthase kinase 3 (Gsk3a-b) inhibitors are pyrrolidindione-based GSK3 inhibitors. "Pyrrolidindione-based GSK3 inhibitor" as used herein relates to selective cell permeable ATP-competitive inhibitors of GSK3α and GSK3β with low IC50 values. In one embodiment the pyrrolidindione-based GSK3 inhibitor is selected from the group comprising 3-(2,4-Dichlorophenyl)-4-(1-methyl-1H-indol-3-yl)-1H-pyrrole-2,5-dione (SB216763), 3-[(3-Chloro-4-hydroxyphenyl)amino]-4-(2-nitrophenyl)-1H-pyrrol-2,5-dione (SB415286), N6-{2-[4-(2,4-Dichlorophenyl)-5-imidazol-1-yl-pyrimidin-2-ylamino]-ethyl-3-nitro-pyridine-2,6-diamine 2HCl, 3-Imidazo[1,2-a]pyridin-3-yl-4-[2-(morpholine-4-carbonyl)-25 1,2,3,4-tetrahydro-[1,4]diazepino[6,7,1-hi]indol-7-yl]-pyrrole-2,5-dione, 9-Bromo-7,12-dihydro-indolo[3,2-d][1]benzazepin-6(5H)-one (Kenpaullone), 9-Bromo-7,12-dihydro-pyrido[3',2':2,3] azepino[4,5-b]indol-6(5H)-one (CHIR99021) and (3-(3-Amino-phenyl)-4-(1-methyl-1H-indol-3-yl)-pyrrole-2,5-dione (CP21R7, also referred to as "compound 21" herein; see e.g. L. Gong et al; Bioorganic & Medicinal Chemistry Letters 20 (2010), 1693-1696). In one embodiment the CDC-like kinase 1 (Clk1-2-4) inhibitor is selected from the group comprising benzothiazole and 3-Fluoro-N-[1-isopropyl-6-(1-methyl-piperidin-4-yloxy)-1,3-dihydro-benzoimidazol-(2E)-ylidene]-5-(4-methyl-1H-pyrazole-3-sulfonyl)-benzamide. In one embodiment the mitogen-activated protein kinase 15 (Mapk15) inhibitor is selected from the group comprising 4-(4-Fluorophenyl)-2-(4-methylsulfinylphenyl)-5-(4-pyridyl)-1H-imidazole (SB203580) and, 5-Isoquinolinesulfonamide (H-89).

In one embodiment the dual-specificity tyrosine-(Y)-phosphorylation regulated kinase 5 (Dyrk1a-b 4) inhibitor is selected from the group comprising 6-[2-Amino-4-oxo-4H-thiazol-(5Z)-ylidenemethyl]-4-(tetrahydro-pyran-4-yloxy)-quinoline-3-carbonitrile.

In one embodiment the smoothened activator is Purmorphamine (2-(1-Naphthoxy)-6-(4-morpholinoanilino)-9-cyclohexylpurine. Examples of modulators of the interaction between β-catenin (or γ-catenin) and the coactivator proteins CBP (CREB binding protein) and p300 (E1A binding protein p300) are IQ-1 (2-(4-Acetyl-phenylazo)-2-[3,3-dimethyl-3,4-dihydro-2H-isoquinolin-(1E)-ylidene]-acetamide, and ICG-001((6S,9aS)-6-(4-Hydroxy-benzyl)-8-naphthalen-1-ylmethyl-4,7-dioxo-hexahydro-15 pyrazino[1,2-a]pyrimidine-1-carboxylic acid benzylamide (WO 2007056593).

In one embodiment the priming medium is a serum free medium supplemented with insulin, transferrin and progesterone. In one embodiment the serum free medium is supplemented with 10-50 μg/ml insulin, 10-100 μg/ml transferrin and 10-50 nM progesterone, preferably 30-50 μg/ml insulin, 20-50 μg/ml transferrin and 10-30 nM progesterone. Examples of serum-free media suitable for priming are N2B27 medium (N2B27 is a 1:1 mixture of DMEM/F12 (Gibco, Paisley, UK) supplemented with N2 and B27 (both from Gibco)), N3 medium (composed of DMEM/F12 (Gibco, Paisley, UK), 25 μg/ml insulin, 50 μg/ml transferrin, 30 nM sodium selenite, 20 nM progesterone, 100 nM putrescine (Sigma)), or 25 NeuroCult® NS-A Proliferation medium (Stemcell Technologies). In one embodiment the priming medium is a serum free medium supplemented with insulin, transferrin, progesterone and a small molecule inhibitor of glycogen synthase kinase 3 (Gsk3a-b).

Preferably the small molecule inhibitor is (3-(3-Amino-phenyl)-4-(1-methyl-1H-indol-3-yl)-pyrrole-2,5-dione, also referred to as CP21R7 therein. In one embodiment the priming medium is a serum-free medium comprising 10-50 μg/ml insulin, 10-100 μg/ml transferrin and 10-50 nM progesterone and 0.5-4 μM CP21R7 (3-(3-Amino-phenyl)-4-(1-methyl-1H-indol-3-yl)-pyrrole-2,5-dione). In one such embodiment the priming medium comprises 1 μM CP21R7. In one embodiment the priming medium of any of the embodiments described herein additionally comprises recombinant bone morphogenic protein-4 (BMP4). In one preferred embodiment the priming medium is a serum-free medium comprising 10-50 μg/ml insulin, 10-100 μg/ml transferrin, 10-50 nM progesterone, 0.5-4 μM CP21R7 (3-(3-Amino-phenyl)-4-(1-methyl-1H-indol-3-yl)-pyrrole-2,5-dione) and 10-50 ng/ml recombinant bone morphogenic protein-4 (BMP4).

In one embodiment step b) of the method described above comprises incubating the cells in a priming medium for at least 3 days (72 hours). In one embodiment step b) of the method described above comprises incubating the cells in a priming medium for 2 to 4 days (48 hours to 96 hours). In another embodiment step b) of the method described above comprises incubating the cells in a priming medium, wherein the priming medium is a serum-free medium supplemented with CP21R7 (3-(3-Amino-phenyl)-4-(1-methyl-1H-indol-3-yl)-pyrrole-2,5-dione). Preferably the priming medium is supplemented with 0.5-4 μM CP21R7 (3-(3-Amino-phenyl)-4-(1-30 methyl-1H-indol-3-yl)-pyrrole-2,5-dione), most preferably 1-2 μM CP21R7 (3-(3-Amino-phenyl)-4-(1-methyl-1H-indol-3-yl)-pyrrole-2,5-dione). In one embodiment the priming medium additionally comprises recombinant bone morphogenic protein-4 (BMP4). In another embodiment step b) of the method described above comprises incubating the cells in a priming medium, wherein the priming medium is a serum-free medium supplemented with CP21R7 (3-(3-Amino-phenyl)-4-(1-methyl-1H-indol-3-yl)-pyrrole-2,5-dione), and incubating the cells for three days (72 hours). In one such embodiment the priming medium additionally comprises recombinant bone morphogenic protein-4 (BMP4).

In another embodiment step b) of the method described above comprises incubating the cells in a priming medium, wherein the priming medium is a serum-free medium supplemented with CP21R7 (3-(3-Amino-phenyl)-4-(1-methyl-1H-indol-3-yl)-pyrrole-2,5-dione), and incubating the cells for 2 to 4 days (48 hours to 96 hours). In one such embodiment the priming medium additionally comprises recombinant bone morphogenic protein-4 (BMP4).

"Induction medium" as used herein refers to any chemically defined medium useful for the induction of primed cells into SIX2 and/or WT1 and/or SALL1 positive renal precursor cells on a monolayer. In one embodiment the renal precursor cells express all three marker genes SIX2, WT1 and SALL1 and are referred to as SWS+ renal precursor cells. In one embodiment the renal precursor cells are metanephric mesenchyme cells. In another embodiment the renal precursor cells downregulate marker genes of the intermediate mesoderm. Hence, in one embodiment the renal precursor cell express PAX2 only at a very low level. In one embodiment the renal precursor cells do not express LIM1 and/or BRY.

Examples of media suitable for the induction are DEMEM/F12, RPMI 1640 (Invitrogen) or William's E Medium (Invitrogen).

In one embodiment the induction medium is supplemented with a Bone morphogenetic protein (BMP), like BMP4, BMP7 or other BMPs like BMP2, BMP3, BMP 5, BMP 6, BMP 8a, BMP 8b, or BMP 9.

Preferably the induction medium is a medium supplemented with BMP7. In one such embodiment the induction medium is supplemented with 20-80 ng/ml BMP7, preferably 50 ng/ml BMP7.

With the new method presented herein it is now possible to differentiate renal precursor cells expressing SIX2 from pluripotent stem cells with a yield of up to 95%. The product of step c) can be easily identified in a cell culture as SIX2 and WT1 and/or SALL1 positive cells.

In one embodiment the induction medium additionally comprises Retinoic acid (RA), like all-trans-Retinoic acid or 9-cis Retinoic acid. In another embodiment the induction medium comprises a Retinoic Acid inhibitor or an Retinoic Acid agonist. Retinoic acid inhibitors and Retinoic acid agonists are well known in the art.

Preferably the induction medium is a medium supplemented with RA. In one such embodiment the induction medium is supplemented with 50-200 nM RA, preferably 100 nM RA.

In one embodiment the induction medium is supplemented with RA and BMP7.

In one embodiment the induction medium additionally comprises 1-5% serum, preferably 2.5% serum. Serum useful therein is for example fetal bovine serum, known in the art. In another embodiment the induction medium is supplemented with amino acids, e.g. non essential Aminoacid solution from Sigma-Aldrich (Catalogue number M7145).

In another embodiment the induction medium additionally comprises beta-mecaptoethanol.

In one embodiment step c) of the method described above comprises incubating the cells in a induction medium for 2 days (48 hours).

In one embodiment, steps a) to c) of the method described above together take six days.

In embodiment the method as described in any the above embodiments is useful for differentiating pluripotent stem cells into podocytes. In one embodiment the method as described in any of the above embodiments additionally comprises step d) incubating the product of step c) under conditions suitable for proliferation of podocytes. Typically, the SWS+ cells obtained in step c) are harvested and expanded in a chemically defined proliferation medium. In one embodiment, step d) comprises incubating the cells obtained in step c) for 24-168 h, preferably for 48-96 hours in a proliferation medium.

Proliferation medium as used herein is a medium supplemented with growth factors and/or small molecules enhancing the proliferation and survival of podocytes cells.

In one embodiment step the proliferation medium is a chemically supplemented medium (SP medium). SP media useful herein are e.g. DMEM/F12 medium (e.g. Invitrogen or Gibco Cat num. 31331-028) or RPMI 1640 (Gibco Cat num. 61870-010) or DMEM medium). In one embodiment the proliferation medium is supplemented with 2-10% serum, for example 2-10% fetal bovine serum. In one embodiment the proliferation medium is supplemented with a Knock-out serum replacement (e.g. from Invitrogen, Catalogue number 10828028).

In another embodiment the proliferation medium is supplemented with 0.1-0.5 mM RA, preferably 0.1 mM RA. In another embodiment the proliferation medium is supplemented with 10-200 nM Vitamin D3, preferably 100 nM Vitamin D3. In one embodiment the proliferation medium is supplemented with both RA and Vitamin D3. In one embodiment the proliferation medium further comprises stable glutamine. In a preferred embodiment the proliferation medium is a DMEM/F12 medium supplemented with 10% serum, 100 nM Vitamin D3 and 0.1 mM Retinoic Acid.

The renal precursor cells and podocytes obtained by the method described herein can be expanded for several passages.

Any of the above embodiments may be present singly or in combination.

In one embodiment of the present invention a method for generating patient specific or healthy individual specific renal precursor cells or podocytes is provided. Towards this end, human induced pluripotent stem cells (iPSCs) obtained from a patient or healthy individual are differentiated into renal precursor cells or podocytes with the method described herein. The patient-specific human iPSCs can be obtained by methods known in the art by reprogramming somatic cells obtained from the patients or healthy individuals to pluripotent stem cells. For example, fibroblast cells, keratinocytes or adipocytes may be obtained by skin biopsy from the individual in need of treatment or from a healthy individual and reprogrammed to induced pluripotent stem cells by the methods known in the art. Other somatic cells suitable as a source for induced pluripotent stem cells are leucocytes cells obtained from blood samples or epithelial cells or other cells obtained from urine samples. The patient specific induced pluripotent stem cells are then differentiated to patient specific or healthy individual specific renal precursor cells or podocytes by the method described herein. In another aspect of the invention, a population of renal precursor cells or podocytes produced by any of the foregoing methods is provided. Preferably, the population of renal precursor cells or podocytes is patient specific, i.e. derived from iPSCs obtained from diseased individuals. In another embodiment the population of renal precursor cells or podocytes is obtained from a healthy individual.

Patient derived renal precursor cell or podocytes represent a disease relevant in vitro model to study the pathophysiology of renal diseases like acute kidney failure/acute kidney injury, Alport syndrome, angiotensin antibodies and focal segmental glomerulosclerosis, APOL1 mutations, CFHR5 nephropathy, Bartter syndrome, collapsing glomerulopathy, diabetes and diabetic kidney disease related to CMV, Fabry's disease, glomerular diseases, HIV-associated nephropathy (HIVAN), lipoprotein glomerulopathy, lupus kidney disease, lupus nephritis, membranoproliferative glomerulonephritis, nodular glomerulosclerosis, post-infectious glomerulonephritis, post-streptococcal glomerulonephritis. In one embodiment the renal precursor cells or podocytes obtained by this method are used for screening for compounds that reverse, inhibit or prevent renal diseases caused by dysfunction of renal cells, e.g. Chronic Kidney Disease (CKD), Focal segmental glomerulosclerosis (FSGS), Membranoproliferative glomerulonephritis, Polycystic kidney disease (PKD) and diabetic nephropathy associated with Diabetes Type-2. Preferably, the renal precursor cells or podocytes obtained by the method of the invention described herein are derived from diseased subjects. In another embodiment the renal precursor cells or podocytes obtained by this method are used for screening and evaluating new targets and compounds for treatment of Diabetes and Diabetic Kidney Disease. Preferably, the renal precursor cells or podocytes obtained by the method of the invention described herein are derived from individuals affected by renal diseases like for example Chronic Kidney Disease (CKD), Focal segmental glomerulosclerosis (FSGS), Membranoproliferative glomerulonephritis, Polycystic kidney disease (PKD) and diabetic nephropathy associated with Diabetes Type-2. Differentiating renal precursor cells and/or podocytes from diseased subjects represents a unique opportunity to early evaluate drug safety in a human background paradigm. In another embodiment the podocytes obtained by this method are used as an in vitro model of the nephron.

The present invention provides a highly efficient method to supply patient specific podocytes or compatible cells from healthy individuals with the same HLA type suitable for transplantation, both derived in xeno-free conditions. "Xeno-free culture conditions" refers to a medium and a substrate for attachment that comprising components only of human and recombinant origin. Thus the risk of contamination with xenopathogens is circumvented and the renal cells are safe for use in regenerative medicine. Differentiation of patient specific induced pluripotent stem cells (iPSCs) into patient specific podocytes with the method described herein represents an easy accessible and reproducible technology to generate autologous sources of podocytes. The use of autologous and/or compatible cells in cell therapy offers a major advantage over the use of non-autologous cells, which are likely to be subject to immunological rejection. In contrast, autologous cells are unlikely to elicit significant immunological responses.

In a further preferred aspect of the invention the generation of a BioBank of patient specific renal precursor cells or podocytes is envisaged. In one embodiment, a BioBank comprising different populations of renal precursor cells or podocytes obtained from healthy individuals and/or patients is generated. The term "BioBank" as used herein means a library of biological samples taken from different individuals or species. The archived collection of specimen and associated data is intended for research purposes with the aim of addressing diseases associated with vascular complications. In another embodiment, the BioBank is used for vascular regenerative medicine approaches.

In another aspect, the invention provides a therapeutic composition comprising renal precursor cells or podocytes produced by any of the foregoing methods or comprising any of the foregoing cell populations. Preferably, the therapeutic compositions further comprise a physiologically compatible solution including, for example, a phosphate-buffered saline with 5% human serum albumin. The therapeutic composition can be used to treat, prevent, or stabilize renal diseases such as for example, Chronic Kidney Disease (CKD), Focal segmental glomerulosclerosis (FSGS), Membranoproliferative glomerulonephritis, Polycystic kidney disease (PKD) and diabetic nephropathy associated with Diabetes Type-2. For example, fibroblast cells, keratinocytes or adipocytes may be obtained by skin biopsy from the individual in need of treatment or from a healthy individual and reprogrammed to induced pluripotent stem cells by the methods known in the art ("Induction of pluripotent stem cells from adult human fibroblasts by defined factors." Takahashi et al., 2007, Cell 131, 861-72). Other somatic cells suitable as a source for induced pluripotent stem cells are leucocytes cells obtained from blood samples or epithelial cells or other cells obtained from urine samples. The patient specific induced pluripotent stem cells are then differentiated to podocytes by the method described herein, harvested and introduced into the individual to treat the condition. The renal precursor cells or podocytes produced by the method of the invention may be used to replace or assist the normal function of diseased or damaged tissue.

Another embodiment of the invention is the use of BioBanks of renal precursor cells or podocytes for therapy of renal diseases. The BioBanks preferably comprise renal precursor cells or podocytes obtained from patients or healthy individuals with several HLA types. Transplanting cells obtained from a healthy donor to an individual in need of treatment with a compatible HLA type obviates the significant problem of rejection reactions normally associated with heterologous cell transplants. Conventionally, rejection is prevented or reduced by the administration of immunosuppressants or anti-rejection drugs such as cyclosporine. However, such drugs have significant adverse side-effects, e.g., immunosuppression, carcinogenic properties, kidney toxicity as well as being very expensive. The present invention eliminates, or at least significantly reduces, the need for anti-rejection drugs, such as cyclosporine, imulan, FK-506, glucocorticoids, and rapamycin, and derivatives thereof.

With respect to the therapeutic methods of the invention, it is not intended that the administration of renal precursor cells or podocytes to a mammal be limited to a particular mode of administration, dosage, or frequency of dosing; the present invention contemplates all modes of administration, including intramuscular, intravenous, intrarticular, intralesional, subcutaneous, or any other route sufficient to provide a dose adequate to prevent or treat a disease. The renal precursor cells or podocytes may be administered to the mammal in a single dose or multiple doses. When multiple doses are administered, the doses may be separated from one another by, for example, one week, one month, one year, or ten years. One or more growth factors, hormones, interleukins, cytokines, small molecules or other cells may also be administered before, during, or after administration of the cells to further bias them towards a particular cell type.

As used herein the term "differentiating", "differentiation" refers to one or more steps to convert a less-differentiated cell into a somatic cell, for example to convert a pluripotent stem cell into renal precursor cells or podocytes. Differentiation of a pluripotent stem cell to renal precursor cells or podocytes is achieved by the method described herein.

The term "stem cell" as used herein refers to a cell that has the ability for self-renewal. An "undifferentiated stem cell" as used herein refers to a stem cell that has the ability to differentiate into a diverse range of cell types. As used herein, "pluripotent stem cells" as used herein refers to a stem cell that can give rise to cells of multiple cell types. Pluripotent stem cells (PSCs) include human embryonic stem cells (hESCs) and human induced pluripotent stem cells (hiPSCs). Human induced pluripotent stem cells can be derived from reprogrammed somatic cells, e.g. by transduction of four defined factors (Sox2, Oct4, Klf4, c-Myc) by methods known in the art. The human somatic cells can be obtained from a healthy individual or from a patient. These donor cells can be easily obtained from any suitable source. Preferred herein are sources that allow isolation of donor cells without invasive procedures on the human body, for example human skin cells, blood cells or cells obtainable from urine samples. Although human pluripotent stem cells are preferred, the method is also applicable to non-human pluripotent stem cells, such as primate, rodent (e.g. rat, mouse, rabbit) and dog pluripotent stem cells.

As used herein, "renal precursor cells" or "cells in a metanephric mesenchyme renal precursor stage" are cells that differentiated into the metanephric mesenchyme stage and express at least the cellular marker SIX2, and in a preferred embodiment also the cellular markers SALL1 and WT1. Renal precursor cells as used herein are characterized by down-regulation of marker genes of the pluripotent stage and the intermediate mesoderm stage, like for example PAX 2, BRY and/or LIM1. These cells have the potential to differentiate into all renal cells, including the ability to give rise to podocytes.

As used herein "intermediate mesoderm cells" are cells that express one or more of the cellular markers BRY, LIM1 and PAX2 and which do not express SIX2, SALL1 and WT1, or only at a very low level.

As used herein "downregulation of a marker" refers to a decrease of an expression level of a marker gene and its gene product. The term can mean that the expression level of a certain marker gene and its gene product in one differentiation stage is decreased compared to another differentiation stage. "Downregulation of a marker" can also refer to a complete abolishment of the expression of a marker gene and its gene product in a cell, e.g. the expression of the marker gene and its gene product is not detectable any more.

As used herein "upregulation of a marker" refers to an increase of an expression level of a marker gene and its gene product. The term can mean that the expression level of a certain marker gene and its gene product in one differentiation stage is increased compared to another differentiation stage. "Upregulation of a marker" can also refer to a an increase of an expression of a marker gene and its gene product from no (detectable) expression to low, medium or high expression of a marker gene and its gene product.

"Expression of marker" means that a certain gene is transcribed into mRNA and usually is subsequently translated into a protein (its gene product) which exerts a certain function in a cell. The expression of a marker can be detected and quantified on the RNA level or on the protein level by methods known in the art. Preferred herein is the detection of the expression of a marker on the protein level, e.g. by testing for the presence of a certain protein with antibodies binding to the marker.

"Podocytes" are a type of cell located in the kidneys and also known as glomerular epithelial cells. Podocytes have a characteristic cell phenotype: They consist of a main body and thin extensions that branch out of it and possess characteristics like long processes, or "foot projections". As used herein "podocytes" are cells that express at least the specific surface marker podocin and the expression of one or more further surface markers/cellular markers selected from the group of α-actinin-4, WT1, synaptopodin or nephrin. Preferred therein are mature podocytes, i.e. podocytes that do not express the marker PAX2.

Podocin is a glomerular protein which plays a role in the regulation of glomerular permeability, and acts as a linker between the plasma membrane and the cytoskeleton. It is encoded by NPHS2 (full name nephrosis 2, idiopathic, steroid-resistant (podocin), NCBI Gene ID 7827, also known as PDCN or SRN1).

Alpha actinins belong to the spectrin gene superfamily which represents a diverse group of cytoskeletal proteins, including the alpha and beta spectrins and dystrophins. Alpha actinin is an actin-binding protein with multiple roles in different cell types. In nonmuscle cells, the cytoskeletal isoform is found along microfilament bundles and adherens-type junctions, where it is involved in binding actin to the membrane. In contrast, skeletal, cardiac, and smooth muscle isoforms are localized to the Z-disc and analogous dense bodies, where they help anchor the myofibrillar actin filaments. This gene encodes a nonmuscle, alpha actinin isoform which is concentrated in the cytoplasm, and thought to be involved in metastatic processes. Mutations in this gene have been associated with focal and segmental glomerulosclerosis. α-actinin-4 is encoded by ACTN4 (full name actinin, alpha 4, NCBI Gene ID 81, also known as FSGS; FSGS1; ACTININ-4).

Synaptopodin is an actin-associated protein that may play a role in actin-based cell shape and motility. The name synaptopodin derives from the protein's associations with postsynaptic densities and dendritic spines and with renal podocytes. The protein is encoded by SYNPO (NCBI Gene ID 11346).

Nephrin is a member of the immunoglobulin family of cell adhesion molecules that functions in the glomerular filtration barrier in the kidney. The gene is primarily expressed in renal tissues, and the protein is a type-1 transmembrane protein found at the slit diaphragm of glomerular podocytes. The slit diaphragm is thought to function as an ultrafilter to exclude albumin and other plasma macromolecules in the formation of urine. It is encoded by Nphs1, also known as CNF, NPHN or nephrin (NCBI Gene ID 4868). Mutations in this gene result in Finnish-type congenital nephrosis 1, characterized by severe proteinuria and loss of the slit diaphragm and foot processes.

As used herein, "renal diseases" relates to any disease caused by injury, loss or dysfunction of renal cells. Examples for renal diseases are Chronic Kidney Disease (CKD), Focal segmental glomerulosclerosis (FSGS), Membranoproliferative glomerulonephritis, Polycystic kidney disease (PKD) and diabetic nephropathy associated with Diabetes Type-2. Further examples are acute kidney failure/acute kidney injury, Alport syndrome, angiotensin antibodies and focal segmental glomerulosclerosis, APOL1 mutations, CFHR5 nephropathy, Bartter syndrome, collapsing glomerulopathy, diabetes and diabetic kidney disease related to CMV, Fabry's disease, glomerular diseases, HIV-associated nephropathy (HIVAN), lipoprotein glomerulopathy, lupus kidney disease, lupus nephritis, membranoproliferative glomerulonephritis, nodular glomerulosclerosis, post-infectious glomerulonephritis, post-streptococcal glomerulonephritis.

References

Batchelder, C. A., Lee, C. C., Matsell, D. G., Yoder, M. C., and Tarantal, A. F. (2009). Renal ontogeny in the rhesus monkey (*Macaca mulatta*) and directed differentiation of human embryonic stem cells towards kidney precursors. Differentiation 78, 45-56.

Ok-Hee Chai, Chang-Ho Song, Sung-Kwang Park, Won Kim and Eui-Sic Cho (2013). Molecular regulation of kidney development. Anat Cell Biol. 2013 March; 46(1): 19-31.

Humphreys, B. D., and Bonventre, J. V. (2007). The contribution of adult stem cells to renal repair. Nephrologie & therapeutique 3, 3-10.

Kim, D., and Dressler, G. R. (2005). Nephrogenic factors promote differentiation of mouse embryonic stem cells into renal epithelia. J Am Soc Nephrol 16, 3527-3534.

Lin, S. A., Kolle, G., Grimmond, S. M., Zhou, Q., Doust, E., Little, M. H., Aronow, B., Ricardo, S. D., Pera, M. F., Bertram, J. F., et al. (2010). Subfractionation of differentiating human embryonic stem cell populations allows the isolation of a mesodermal population enriched for intermediate mesoderm and putative renal progenitors. Stem cells and development 19, 1637-1648.

Mae, S., Shirasawa, S., Yoshie, S., Sato, F., Kanoh, Y., Ichikawa, H., Yokoyama, T., Yue, F., Tomotsune, D., and Sasaki, K. (2010). Combination of small molecules enhances differentiation of mouse embryonic stem cells into intermediate mesoderm through BMP7-positive cells. Biochemical and biophysical research communications 393, 877-882.

Mae, S., Shono, A., Shiota, F., Yasuno, T., Kajiwara, M., Gotoda-Nishimura, N., Arai, S., Sato-Otubo, A., Toyoda, T., Takahashi, K., et al. (2013). Monitoring and robust induction of nephrogenic intermediate mesoderm from human pluripotent stem cells. Nat Commun 4, 1367.

Morizane, R., Monkawa, T., and Itoh, H. (2009). Differentiation of murine embryonic stem and induced pluripotent stem cells to renal lineage in vitro. Biochemical and biophysical research communications 390, 1334-1339.

Narayanan, K., Schumacher, K. M., Tasnim, F., Kandasamy, K., Schumacher, A., Ni, M., Gao, S., Gopalan, B., Zink, D., and Ying, J. Y. (2013). Human embryonic stem cells differentiate into functional renal proximal tubular-like cells. Kidney international 83, 593-603.

Ryuichi Nishinakamura, Yukako Uchiyama, Masaji Sakaguchi, Sayoko Fujimura (2011), Nephron progenitors in the metanephric mesenchyme. Pediatric Nephrology, Volume 26, Issue 9, pp 1463-1467

Nishikawa, M., Yanagawa, N., Kojima, N., Yuri, S., Hauser, P. V., and Jo, O. D. (2012). Stepwise renal lineage differentiation of mouse embryonic stem cells tracing in vivo development. Biochemical and biophysical research communications 417, 897-902.

Ren, X., Zhang, J., Gong, X., Niu, X., Zhang, X., and Chen, P. (2010). Differentiation of murine embryonic stem cells toward renal lineages by conditioned medium from ureteric bud cells in vitro. Acta biochimica et biophysica Sinica 42, 464-471.

Song, B., Smink, A. M., Jones, C. V., Callaghan, J. M., Firth, S. D., Bernard, C. A., Laslett, A. L., Kerr, P. G., and Ricardo, S. D. (2012). The directed differentiation of human iPS cells into kidney podocytes. PloS one 7, e46453.

Tan, P. P., and Loebel, D. A. (2007). Gene function in mouse embryogenesis: gene set for gastrulation. Nat Rev Genet 8, 368-381.

Tiscornia, G., Vivas, E. L., and Belmonte, J. C. (2011). Diseases in a dish: modeling human genetic disorders using induced pluripotent cells. Nature Med 17, 1570-1576.

Wiggins, R. C. (2007). The spectrum of podocytopathies: a unifying view of glomerular diseases. Kidney international 71, 1205-1214.

EXAMPLES

Materials and Methods

CP21R7: 3-(3-Amino-phenyl)-4-(1-methyl-1H-indol-3-yl)-pyrrole-2,5-dione (also referred to as "compound 21" herein; see e.g. L. Gong et al; Bioorganic & Medicinal Chemistry Letters 20 (2010), 1693-1696).

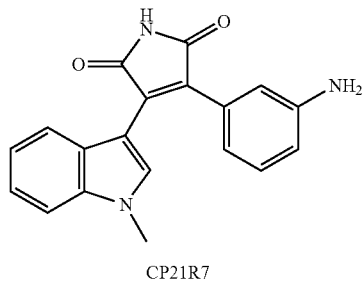 [SMILES: Cn1cc(C2=C(c3cccc(N)c3)C(=O)NC2=O)c2ccccc21]

CP21R7

Cell Culture:

Pluripotency Medium: TeSR1 supplemented with Y27632 ROCK Kinase inhibitor (commercially available, e.g. Catalogue Number: 1254 from Tocris bioscience).

Priming Medium: 1:1 mixture of DMEM:F12 (1:1) plus GlutaMAX™ (Invitrogen) and Neurobasal media (N2B27 medium) with N2 and B27 supplements (all Invitrogen), with 1 µM CP21R7 (Roche) and 25 ng/ml BMP4 (Peprotech).

Induction Medium: DMEM:F12 plus GlutaMAX™ (Invitrogen) medium supplement with 2.5% FBS (Life technologies) 0.1 mM non essential amino acid mix (NEAA), 0.1 mM b-ME, 100 nM Retinoic Acid (Sigma) and 50 ng/ml BMP7 (Prepotech).

Podocytes Proliferation Medium: DMEM:F12 plus GlutaMAX™ (Invitrogen) supplemented with 10% FBS (Invitrogen), 0.1 mM Retinoic Acid (Sigma) and 100 nM Vitamin D3 (Sigma).

Human ESCs: SA001, LOT CA001 were isolated on Mar. 20, 2001 at Göteborg University and Cellartis AB Arvid Wallgrens Backe 20, SE-413 46 Göteborg, SWEDEN follows all applicable laws in Sweden and is approved by the Local Research Ethics Committees at Göteborg University and Uppsala University. Embryo source: Frozen, surplus from IVF. Donor confidentiality: In order to protect the privacy and the confidentiality of the donors, all identifiers associated with the embryo donors have been removed. Thus, no information about the donors is accessible. Notably, the donation did not result in any financial gain for the donors. We have the approval to work with hESCs and to derive different cell lines. The responsible ethical committee (Ethikkommission beider Basel) and the Federal office of public health have approved our research project. (Ref-No: R—FP-S-1-0002-0000).

Human iPSCs: Catalogue Number: SC101A-1 Lot. Number 110218-FF from SBI System Biosciences/Catalogue Number: A13777 from Life technologies Gibco® Episomal hiPSC Line.

Human pluripotent stem cells are routinely cultured on hESC-qualified Matrigel® (BD Bioscience) in TeSR1 medium (Stem cell Technologies). Cultures are passaged every 4-6 days using StemPro® Accutase® (Invitrogen). For an increased viability TeSR1 medium is supplemented with 10 µM ROCK-inhibitor one hour prior enzymatic dissociation.

1. Method for Differentiation of Pluripotent Stem Cells into Podocytes (i) Before the enzymatic dissociation of hPSC colonies using StemPro® Accutase® (Invitrogen) cells were preincubated for one hour with 10 µM ROCK-Inhibitor Y27632. 37.000 single hPSCs per cm' were plated onto growth factor reduced Matrigel® (BD bioscience) coated cell culture plates in TeSR1 medium supplemented with 10 µM ROCK-30 Inhibitor.

(ii) On day 1 attachment medium was exchanged to N2B27 (Gibco) medium supplemented with 1 µM Compound 21 (CP21R7) and 25 ng/ml BMP4 (R&D Systems). Cells were cultivated for additional 3 days without media change.

(iii) On day 4 the priming medium was exchanged to DMEMF12 (Gibco) medium supplemented with 100 nM retinoic acid (Sigma, R2625) and 50 ng/ml BMP7 (Peprotech). Cells were cultivated for additional 2 days without media change.

(vi) On day 6 the cells were dissociated with Accutase® solution and plated on collagen I coated plates at a density of 40000-50000 cells/cm' in DMEMF12 (Gibco) medium supplemented with 0.1 mM retinoic acid (Sigma, 82625) and 100 nM Vitamin D3 (Sigma) for another 7 days. The proliferation medium was changed every other day.

2. Immunocytochemistry Analysis and Image Based High Content Analysis (HCA) for Quantification The cells were fixed with PBS containing 4% paraformaldehyde for 20 min at room temperature. After three washing with PBS the cells the cells were then blocked with 5% BSA solution (Blocking buffer) for 60 min. When probing for an intracellular antigen, 0.5% Triton-X was included in the blocking buffer. The samples were stained with the primary antibody diluted in 2% BSA solution overnight at 4° C., followed by incubation with the appropriated secondary antibody for 1 h at room temperature. Nuclei were stained by DAPI for 5 minutes at room temperature. Fluorescence was acquired and analyzed by the Operetta® High Content Imaging System (PerkinElmer) followed by computer-based image analysis (ImageJ, Java-based image processing program). Separate images from the same field were acquired using appropriate filters, and exported as jpg files.

| Table with primary antibody used in the work. | | |
|---|---|---|
| Antigen | Origin | Catalog Number |
| Bry | R&D System | AF2085 |
| PAX2 | Invitrogen | 716000 |
| LIM1 | Abeam | Ab14554 |
| SIX2 | Proteintech | 11562-1-AP |

-continued

Table with primary antibody used in the work.

| Antigen | Origin | Catalog Number |
| --- | --- | --- |
| WT1 | R&D System | AF5729 |
| SALL1 | R&D System | PP-K9814-00 |
| Actinin-4 | Origene | TA307264 |
| Podocin | Sigma-aldrich | P0372 |
| Synaptopodin | Abeam | Ab101883 |
| ZO-1 | Invitrogen | 61-7300 |
| P-cad | R&D System | MAB861 |
| AQP1 | Santa-Cruz | sc-20810 |

3. Functional Characterization of iPSCs-Derived Podocytes Cells

In response to proinflammatory stimuli Podocytes express specific cytokines including IL-8, Rantes, MIP-1b and MCP1. Bio-Plex Pro™ Cytokine, Chemokine and Growth factor assay (Biorad, M50-0KCAF0Y). After overnight serum starvation hiPS derived podocytes were exposed at two different concentrations of TNFα (1 and 5 ng/ml) for 24 hours. After treatment the supernatants were collected and used to quantify the Cytokine, Chemokine and Growth factor release using Bio-Plex Pro™ Cytokine, Chemokine and Growth factor assay kit (Biorad, M50-0KCAF0Y). The assay was performed following the manufacturer's instruction. To determine whether the differentiation system generates bona fide Podocytes, we challenged the iPS-derived Podocytes with proinflammatory TNFα and analyzed for cytokine and chemokine release. Secretome analysis clearly showed an increase of the supernatant concentration of IL-8, Rantes, MIP-1b and MCP1 in a dose dependent manner, upon TNF-α treatment (FIGS. 8a, 8b, 8c and 8d) comparable to primary human podocytes (Saleem et al., JASN, 2002; data not shown).

The invention claimed is:

1. A method for differentiating human or mouse pluripotent stem cells into renal precursor cells expressing SIX2, WT1 and SALL1, the method comprising the steps of:
    a) providing a monolayer of human or mouse pluripotent stem cells in a pluripotency medium,
    b) incubating the cells of step a) in an adherent culture for at least three days in a medium supplemented with 3-(3-amino-phenyl)-4-(1-methyl-1H-indol-3-yl)-pyrrole-2,5-dione and recombinant bone morphogenic protein-4 (BMP4), and
    c) differentiating the cells of step b) in a serum-free medium supplemented with recombinant bone morphogenic protein-7 (BMP7) and retinoic acid, to produce renal precursor cells expressing SIX2, WT1 and SALL1.

2. The method of claim 1, wherein the pluripotency medium of step a) is a serum-free medium supplemented with an inhibitor of the Rho-associated coiled-coil forming protein serine/threonine kinase family of protein kinases (ROCK kinase inhibitor).

3. The method of claim 2, wherein the ROCK kinase inhibitor is selected from the group consisting of 1-(5-Isoquinolinesulfonyl) homopiperazine, N-Benzyl-2-(pyrimidin-4-ylamino) thiazole-4-carboxamide, and (+)-(R)-trans-4-(1-aminoethyl)-N-(4-pyridyl) cyclohexanecarboxamide dihydrochloride).

4. The method of claim 1, wherein the medium of step b) is a serum free medium supplemented with insulin, transferrin and progesterone.

5. The method of claim 1, wherein step a) comprises incubating the cells in the pluripotency medium for 18 hours to 30 hours.

6. The method of claim 1, wherein step b) comprises incubating the cells in the medium for 3 to 4 days.

7. The method of claim 1, wherein step c) comprises incubating the cells in the medium for 18 hours to 48 hours.

8. The method of claim 1, wherein the pluripotent stem cell is an induced pluripotent stem cell.

9. The method claim 8, wherein the induced pluripotent stem cell is obtained from a subject suffering from a renal disease.

10. A method for differentiating human or mouse pluripotent stem cells into renal precursor cells expressing SIX2, WT1 and SALL1, the method comprising the steps of:
    a) providing a monolayer of human or mouse pluripotent stem cells in a pluripotency medium,
    b) incubating the cells of step a) in an adherent culture for at least three days in a medium supplemented with 3-(3-amino-phenyl)-4-(1-methyl-1H-indo-1-3-yl)-pyrrole-2,5-dione and recombinant bone morphogenic protein-4 (BMP4),
    c) differentiating the cells of step b) in a serum-free medium supplemented with recombinant bone morphogenic protein-7 (BMP7) and retinoic acid, to produce renal precursor cells expressing SIX2, WT1 and SALL1, and
    d) incubating the renal precursor cells of step c) in a medium comprising retinoic acid and vitamin D3 to obtain proliferating podocytes.

11. The method of claim 10, wherein the medium of step d) is supplemented with 10-200 nM vitamin D3.

* * * * *